US012371445B2

(12) United States Patent
Waldmann et al.

(10) Patent No.: US 12,371,445 B2
(45) Date of Patent: *Jul. 29, 2025

(54) HETEROAROMATIC SILICON-FLUORIDE-ACCEPTORS USEFUL FOR $^{18}$F LABELING OF MOLECULES AND BIOMOLECULES, AND METHODS OF PREPARING SAME

(71) Applicants: THE REGENTS OF THE UNIVERSITY OF CALIFORNIA, Oakland, CA (US); CALIFORNIA INSTITUTE OF TECHNOLOGY, Pasadena, CA (US)

(72) Inventors: Christopher Martin Waldmann, Santa Monica, CA (US); Anton A. Toutov, Magnolia, TX (US); Jennifer Marie Murphy, Los Angeles, CA (US); Robert H. Grubbs, South Pasadena, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 17/933,234

(22) Filed: Sep. 19, 2022

(65) Prior Publication Data

US 2023/0114064 A1 Apr. 13, 2023

Related U.S. Application Data

(60) Continuation of application No. 16/997,240, filed on Aug. 19, 2020, now Pat. No. 11,447,508, which is a division of application No. 15/575,979, filed as application No. PCT/US2016/033923 on May 24, 2016, now Pat. No. 10,800,797.

(60) Provisional application No. 62/166,240, filed on May 26, 2015.

(51) Int. Cl.
*C07F 7/12* (2006.01)
*A61K 51/10* (2006.01)
*C07B 59/00* (2006.01)

(52) U.S. Cl.
CPC ............ *C07F 7/12* (2013.01); *A61K 51/1027* (2013.01); *A61K 51/1072* (2013.01); *C07B 59/004* (2013.01); *C07B 2200/05* (2013.01)

(58) Field of Classification Search
CPC ............ C07F 7/12; C07B 59/00; A61K 51/00
See application file for complete search history.

(56) References Cited

U.S. PATENT DOCUMENTS

| 7,067,676 B2 | 6/2006 | Dell et al. |
| 11,447,508 B2* | 9/2022 | Waldmann ............ C07B 59/004 |
| 2009/0035215 A1* | 2/2009 | Srinivasan ......... A61K 51/0491 |
| | | 424/1.89 |
| 2018/0346491 A1 | 12/2018 | Waldmann et al. |

FOREIGN PATENT DOCUMENTS

| JP | 2017-548194 A | 8/2018 |
| JP | 2018-521956 A | 8/2018 |
| WO | 2008/040441 A2 | 4/2008 |
| WO | 2012/087908 A1 | 6/2012 |

OTHER PUBLICATIONS

Baum et al., "Lithium-silylindolide als Precursor fur 1, 2-, 1,3-Bis(sily)indole und Bis(indol-1, 3-yl)silane", Zeitschrift fur Anorganische und Allgemeine Chemie, 1999, vol. 625, No. 12, pp. 1969-1978.
Braun et al., "Reactivity of a Palladium Fluoro Complex Towards Silanes and Bu3SnCH=CH2: Catalytic Derivatisation of Pentafluoropyridine Based on Carbon-Fluorine Bond Activation Reactions", Dalton Transactions, 2006, pp. 5118-5123.
Calle et al., "Synthesis and Reactions of Silylated and Stannylated 1,2-Azoles", Synthesis, 2001, No. 13, pp. 1949-1958.
Dialer et al., "Studies Toward Development of New Silicon-Containing Building Blocks for the Direct 18-F Labeling of Peptides", Journal of Medicinal Chemistry, 2013, vol. 56, No. 19, pp. 7552-7563.
Frenzel et al., Indolyl- and Pyrrolylsilances—Syntheses and Crystal Structures:, Zeitschrift fur Naturforschung B, 1995, vol. 50, No. 11, pp. 1658-1664.
Frenzel et al., "New Routes to 1,2- and 1,3-Bis(silyl)indoles—Synthesis of the first Bis(indol-3-yl)silane", Main Group Chemistry, 1996, vol. 1, pp. 399-408.
Kang, Cross-Coupling and Carbonylative Cross-Coupling of Organofluorosilanes With Hypervalent Iodonium Tetrafluoroborates, Tetrahedron, 1997, vol. 53, No. 9, pp. 3027-3034.
Klingebiel et al., "Mono-, Bis-, Tris- und Tetrakis(indol-1-yl)silane", Journal of Organometallic Chemistry, 1993, vol. 55, pp. 51-55.
Koudih et al., "Automated Radiosynthesis of N-succinimidyl 3-(di-tert-butyl [18F] fluorosilyl) benzoate ([18F] SiFB) for Peptides and Proteins Radiolabeling for Positron Emission Tomography," Applied Radiation and Isotopes, vol. 89, 2014, pp. 146-150.

(Continued)

*Primary Examiner* — Michael G. Hartley
*Assistant Examiner* — Jagadishwar R Samala
(74) *Attorney, Agent, or Firm* — BakerHostetler

(57) ABSTRACT

The present disclosure sets forth novel compounds and compositions including heteroaromatic silicon-fluoride-acceptors, which are useful for PET scanning. The present disclosure further includes novel methods of $^{18}$F imaging for PET scanning, the methods comprising the preparation of conjugates and bioconjugates of biological ligands of interest with heteroaromatic silicon-fluoride-acceptors. In certain embodiments the invention is practiced in the form of a kit.

15 Claims, 5 Drawing Sheets

(56) References Cited

OTHER PUBLICATIONS

Litau et al., "Next Generation of SiFA/ in-Based TATE Derivatives for PET Imaging of SSTR-Positive Tumors: Influence of Molecular Design on In Vitro SSTR Binding and In Vivo Pharmacokinetics," Bioconjugate Chemistry, vol. 26, No. 12, 2015, pp. 2350-2359.

Nuegebauer et al., Silylfurans and Bis(sily)butadiyes—Synthesis, Lithium Derivatives, Crystal Structure, Zeitschrift fur Naturforshung B, 2000, vol. 55, No. 10, pp. 913-923.

Toutov et al., "Silylation of C—H bonds in aromatic heterocycles by an Earth-abundant metal catalyst", Nature, 2015, vol. 518, pp. 80-84.

Wangler et al., "Kit-Like 18F-Labeling of Proteins: Synthesis of 4-(Di-tertbutyl[ 18F]fluorosilyl)benzenethiol (Si[18F]FA-SH) Labeled Rat Serum Albumin for Blood Pool Imaging with PET", Bioconjugate Chemistry, 2009, vol. 20, pp. 317-321.

Cai et al., "PET Imaging of Colorectal Cancer in Xenograft-Bearing Mice by Use of an 18F-Labeled T84.66 Anti-Carcinoembryonic Antigen Diabody", J. Nucl. Med., 2007, 48, 304.

Cheng et al., "Small-Animal PET Imaging of Human Epidermal Growth Factor Receptor Type 2 Expression with Site-Specific 18F-Labeled Protein Scaffold Molecules", J. Nucl. Med., 2008, 49, 804-813.

Kostikov et al., "Synthesis of [18F]SiFB: a prosthetic group for direct protein radiolabeling for application in positron emission tomography", Nature Protocols, 2012, 7, 1956-1963.

Liu et al., "Microfluidic-Based 18F-Labeling of Biomolecules for Immuno-Positron Emission Tomography", Mol. Imaging, 2011, 10, 168-176.

Olafsen et al., "ImmunoPET using engineered antibody fragments: fluorine-18 labeled diabodies for same-day imaging", Tumor Biol., 2012, 33, 669-677.

Wangler et al., "Silicon-[18F]Fluorine Radiochemistry: Basics, Applications and Challenges", Appl. Sci., 2012, 2, 277-302.

* cited by examiner

HETEROAROMATIC SILICON-FLUORIDE-ACCEPTORS USEFUL FOR $^{18}$F LABELING OF MOLECULES AND BIOMOLECULES, AND METHODS OF PREPARING SAME

CROSS REFERENCE TO RELATED APPLICATIONS

This application is a continuation of U.S. patent application Ser. No. 16/997,240, filed Aug. 19, 2020, which is a divisional of U.S. patent application Ser. No. 15/575,979, filed Nov. 21, 2017, now U.S. Pat. No. 10,800,797, which is a National Stage Entry of International Patent Application No. PCT/US2016/033923, filed May 24, 2016, that claims priority from U.S. Provisional Patent Application Ser. No. 62/166,240, filed May 26, 2015, the entire contents of all of which are incorporated herein by reference in their entireties for all purposes.

GOVERNMENT RIGHTS

This invention was made with government support under Grant No. CHE1212767 awarded by The National Science Foundation. The government has certain rights in the invention.

TECHNICAL FIELD

The present disclosure is directed to novel compounds and compositions comprising heteroaromatic Silicon-Fluoride-Acceptors, which are useful for PET scanning and methods for using these compounds and compositions in PET scanning

BACKGROUND

The most common $^{18}$F-labeling method for biomolecules to date, utilizes $^{18}$F-SFB, a radiolabeled prosthetic group that reacts with the ε-amino group of surface-exposed lysine residues (Liu et al., 2011, Mol. Imaging 10:168; Cai et al., 2007, J. Nucl. Med. 48:304; Olafsen et al., 2012, Tumor Biol. 33:669). In addition, site-specific conjugation using 4-$^{18}$F-fluorobenzaldehyde ($^{18}$F-FBA) has also been demonstrated (Cheng et al., 2008, J. Nucl. Med. 49:804). While $^{18}$F-SFB has been successfully used to generated $^{18}$F-labeled proteins and peptides, labeling with $^{18}$F-SFB is far from ideal; in addition to its unselective conjugation, its 3-step synthesis and subsequent protein conjugation results in very poor decay-corrected radiochemical yields of 1.4-2.5%.

Silicon fluoride acceptors (SiFAs) are under study as new imaging agents useful for positron emission tomography (PET; Wängler et al., 2012, Appl. Sci., 2:277-302). They can be labeled with the radioisotope fluorine-18 via a fast and mild $^{18}$F-$^{19}$F isotopic exchange reaction (IEX; Kostikov et al., 2012, Nature Protocols, 7:1956-1963). However, the application of silicon-fluoride-acceptor-based PET probes has been hampered by their high intrinsic lipophilicity, originating from bulky tert-butyl groups required for in vivo stabilization of the Si-$^{18}$F bond. The problems associated with currently known silicon-fluoride-acceptor-imaging probes in preclinical investigations are poor in vivo stability and unfavorable pharmacokinetic behavior.

There is a need in the art for novel precursors for $^{18}$F-labeled compounds, novel $^{18}$F-labeled compounds, and methods for preparing and using thereof. The present invention addresses this unmet need.

SUMMARY

The present invention relates to a compound of Formula 1:

Formula 1 wherein in Formula 1,
F is selected from the group consisting of $^{19}$F and $^{18}$F;
$A^1$ is a monocyclic or bicyclic heteroaryl ring optionally substituted with 0-4 $R^a$ groups;
$R^a$ is selected, at each independent occurrence, from the group consisting of null, H, F, Cl, Br, I, CN, $NO_2$, $OR^c$, $OC(=O)R^c$, $OC(=O)OR^c$, $OC(=O)NR^cR^d$, $CR^cR^d$, $COR^c$, $C(=O)R^c$, $C(=O)NR^cR^d$, $C(=O)OR^e$, $NR^cR^d$, $NR^cC(=O)R^d$, $NR^cC(=O)OR^d$, $NR^cC(=O)NR^dR^e$, $NR^cS(=O)_2R^d$, $NR^cS(=O)_2NR^dR^e$, $SR^c$, $S(=O)R^c$, $S(=O)_2R^c$, and $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^c$, $OC(=O)R^c$, $OC(=O)OR^c$, $OC(=O)NR^cR^d$, $CR^cR^d$, $COR^c$, $C(=O)R^c$, $C(=O)NR^cR^d$, $C(=O)OR^c$, $NR^cR^d$, $NR^cC(=O)R^d$, $NR^cC(=O)OR^d$, $NR^cC(=O)NR^dR^e$, $NR^cS(=O)_2R^d$, $NR^cS(=O)_2NR^dR^e$, $SR^c$, $S(=O)R^c$, $S(=O)_2R^c$, and $S(=O)_2NR^cR^d$, or independent $R^a$ groups can optionally be joined to form additional rings;
$R^c$, $R^d$ and $R^e$ are selected, at each independent occurrence, from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and any of $R^c$, $R^d$ or $R^e$ can optionally be joined to form additional rings; and
$R^1$ and $R^2$ are each independently an alkyl group.

In one embodiment, $A^1$ is selected from the group consisting of indole, 7-azaindole, benzothiophene, furan, pyrrole, pyrazole, imidazole, and pyridine. In another embodiment, $R^1$ and $R^2$ are tert-butyl groups. In another embodiment, $A^1$ is selected from the group consisting of indole, 7-azaindole, benzothiophene, furan, pyrrole, pyrazole, imidazole, and pyridine, and $R^1$ and $R^2$ are tert-butyl groups. In another embodiment, the compound is selected from the group consisting of:

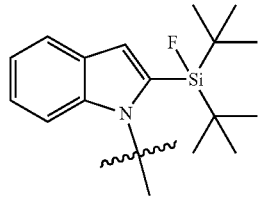

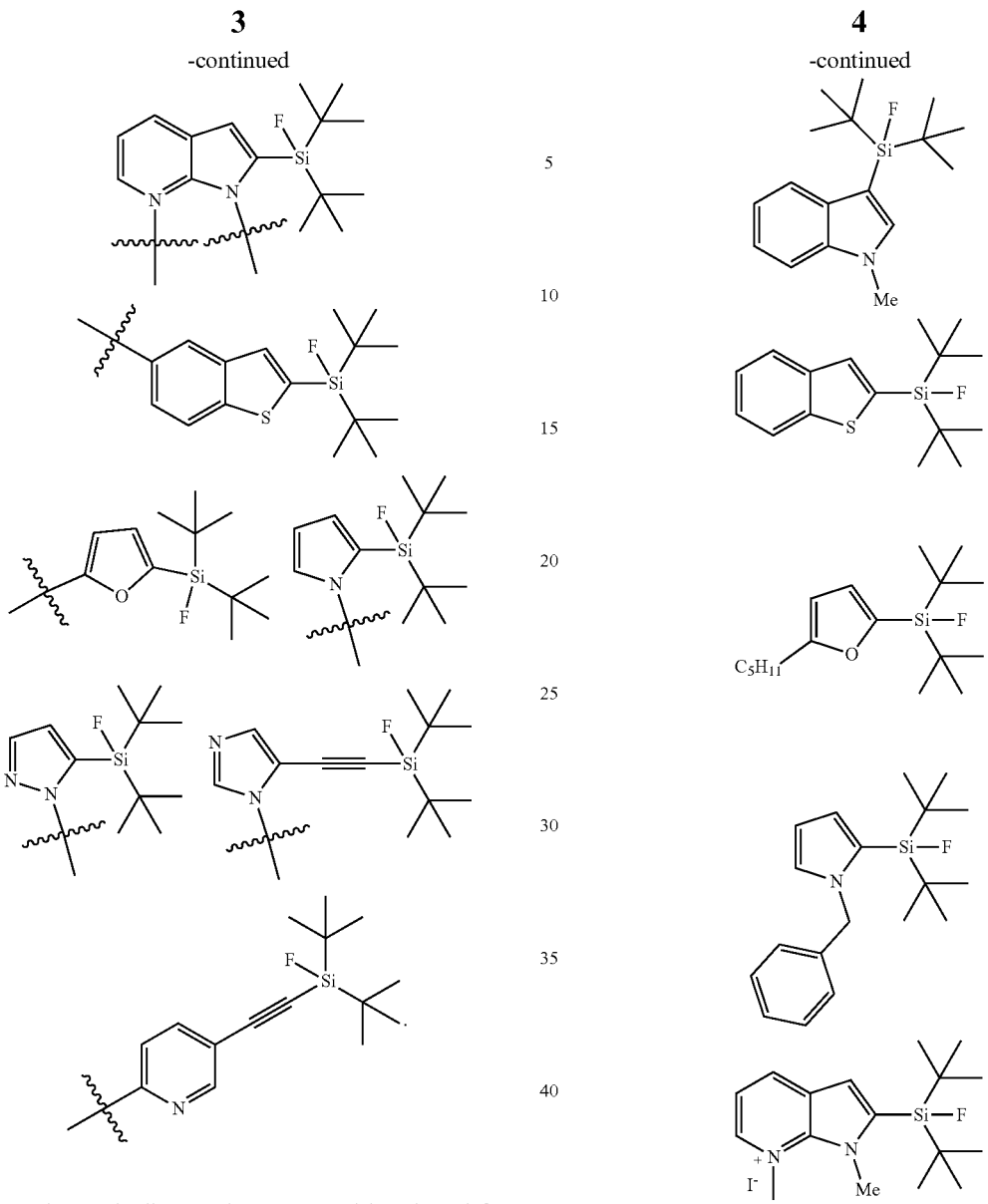

In another embodiment, the compound is selected from the group consisting of:

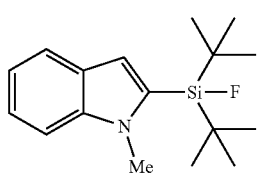

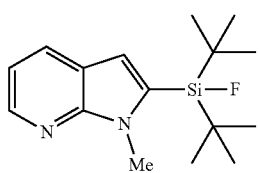

The present invention also relates to a compound of Formula 2:

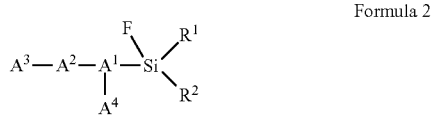

Formula 2 wherein in Formula 2,

F is selected from the group consisting of $^{19}F$ and $^{18}F$;

$A^1$ is a monocyclic or bicyclic heteroaryl ring optionally substituted with 0-4 $R^a$ groups;

$A^2$ is a linker;

$A^3$ is a moiety capable of chemical conjugation or bio-conjugation;

$A^4$ is a moiety comprising a polar auxiliary that may optionally contain a charge;

$R^a$ is selected, at each independent occurrence, from the group consisting of null, H, F, Cl, Br, I, CN, $NO_2$, $OR^c$, $OC(=O)R^c$, $OC(=O)OR^c$, $OC(=O)NR^cR^d$, $CR^cR^d$, $COR^c$, $C(=O)R^c$, $C(=O)NR^cR^d$, $C(=O)OR^c$, $NR^cR^d$, $NR^cC(=O)R^d$, $NR^cC(=O)OR^d$, $NR^cC(=O)NR^dR^e$, $NR^cS(=O)_2R^d$, $NR^cS(=O)_2NR^dR^e$, $SR^c$, $S(=O)R^c$, $S(=O)_2R^c$, and $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^c$, $OC(=O)R^c$, $OC(=O)OR^c$, $OC(=O)NR^cR^d$, $CR^cR^d$, $COR^c$, $C(=O)R^c$, $C(=O)NR^cR^d$, $C(=O)OR^c$, $NR^cR^d$, $NR^cC(=O)R^d$, $NR^c(=O)OR^d$, $NR^cC(=O)NR^dR^e$, $NR^cS(=O)_2R^d$, $NR^cS(=O)_2NR^dR^e$, $SR^c$, $S(=O)R^c$, $S(=O)_2R^c$, and $S(=O)_2NR^cR^d$, or independent $R^a$ groups can optionally be joined to form additional rings;

$R^c$, $R^d$ and $R^e$ are selected, at each independent occurrence, from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and any of $R^c$, $R^d$ or $R^e$ can optionally be joined to form additional rings; and $R^1$ and $R^2$ are each independently an alkyl group.

In one embodiment, $A^1$ is selected from the group consisting of indole, 7-azaindole, benzothiophene, furan, pyrrole, pyrazole, imidazole, and pyridine. In another embodiment, $R^1$ and $R^2$ are tert-butyl groups. In another embodiment, $A^1$ is selected from the group consisting of indole, 7-azaindole, benzothiophene, furan, pyrrole, pyrazole, imidazole, and pyridine, and $R^1$ and $R^2$ are tert-butyl groups. In another embodiment, $A^2$ includes at least one of an unsubstituted alkyl, an unsubstituted polyethylene glycol (PEG), and a bisubstituted triazole. In another embodiment, $A^3$ is selected from the group consisting of an N-hydroxysuccinimide (NHS) ester and maleimide.

In one embodiment, the compound of Formula 2 is a compound of Formula 3:

wherein in Formula 3,
m and n are each independently an integer selected from the group consisting of 0, 1, 2, 3, 4, 5, and 6. In another embodiment, m=2 and n=3.

The present invention also relates to a compound of Formula 4:

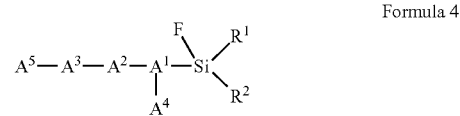

Formula 4 wherein in Formula 4,
F is selected from the group consisting of $^{19}F$ and $^{18}F$;
$A^1$ is a monocyclic or bicyclic heteroaryl ring optionally substituted with 0-4 $R^a$ groups;
$A^2$ is a linker;
$A^3$ is a moiety capable of chemical conjugation or bioconjugation;
$A^4$ is a moiety comprising a polar auxiliary that may optionally contain a charge;
$A^5$ is a moiety comprising a disease targeting molecule or biomolecule;
$R^a$ is selected, at each independent occurrence, from the group consisting of null, H, F, Cl, Br, I, CN, $NO_2$, $OR^c$, $OC(=O)R^c$, $OC(=O)OR^c$, $OC(=O)NR^cR^d$, $CR^cR^d$, $COR^c$, $C(=O)R^c$, $C(=O)NR^cR^d$, $C(=O)OR^c$, $NR^cR^d$, $NR^cC(=O)R^d$, $NR^cC(=O)OR^d$, $NR^cC(=O)NR^dR^e$, $NR^cS(=O)_2R^d$, $NR^cS(=O)_2NR^dR^e$, $SR^c$, $S(=O)R^c$, $S(=O)_2R^c$, and $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^c$, $OC(=O)R^c$, $OC(=O)OR^c$, $OC(=O)NR^cR^d$, $CR^cR^d$, $COR^c$, $C(=O)R^c$, $C(=O)NR^cR^d$, $C(=O)OR^c$, $NR^cR^d$, $NR^cC(=O)R^d$, $NR^cC(=O)OR^d$, $NR^cC(=O)NR^dR^e$, $NR^cS(=O)_2R^d$, $NR^cS(=O)_2$

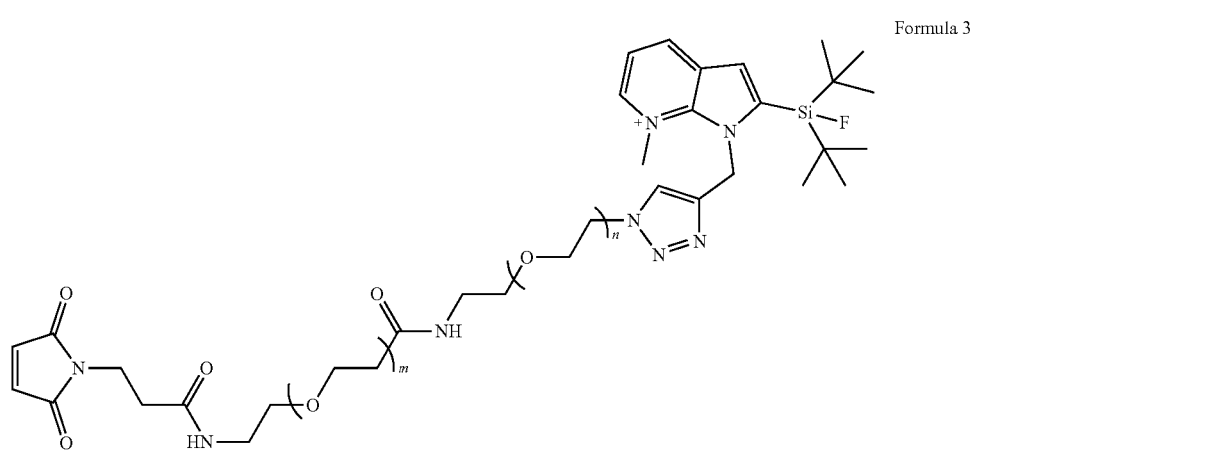

Formula 3

NR$^d$R$^e$, SR$^c$, S(=O)R$^c$, S(=O)$_2$R$^c$, and S(=O)$_2$ NR$^c$R$^d$, or independent R$^a$ groups can optionally be joined to form additional rings;

R$^c$, R$^d$ and R$^e$ are selected, at each independent occurrence, from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and any of R$^c$, R$^d$ or R$^e$ can optionally be joined to form additional rings; and R$^1$ and R$^2$ are each independently an alkyl group.

In one embodiment, A$^1$ is selected from the group consisting of indole, 7-azaindole, benzothiophene, furan, pyrrole, pyrazole, imidazole, and pyridine. In another embodiment, R$^1$ and R$^2$ are tert-butyl groups. In another embodiment, A$^1$ is selected from the group consisting of indole, 7-azaindole, benzothiophene, furan, pyrrole, pyrazole, imidazole, and pyridine, and R$^1$ and R$^2$ are tert-butyl groups. In another embodiment, A$^2$ includes at least one of an unsubstituted alkyl, an unsubstituted polyethylene glycol (PEG), or a bisubstituted triazole. In another embodiment, A$^3$ is selected from the group consisting of an NHS ester, a maleimide, an amide, and a maleimide-thiol adduct.

The invention also relates to a method for imaging a biological target by PET scanning. The method includes the step of introducing into the target an imaging agent. In one embodiment, the imaging agent includes a compound of Formula 1, and a ligand for the target. In one embodiment, F in Formula 1 is $^{18}$F. In another embodiment, the ligand is a disease targeting molecule or biomolecule. In another embodiment, the ligand is a peptide. In another embodiment, the ligand is a protein. In another embodiment, the ligand is an enzyme. In another embodiment, the ligand is an antibody. In another embodiment, the ligand is a small molecule.

In another embodiment, the imaging agent is obtained by site-selective chemical conjugation of the ligand with the compound. In one embodiment, conjugation of the ligand occurs via a thiol group. In another embodiment, conjugation of the compound occurs via a N-hydroxysuccinimide (NHS) ester, a maleimide, or a click chemistry adduct.

The present invention also relates to a kit for $^{18}$F-labeling of a compound of the invention. In one embodiment, the compound is a compound of Formula 1. In one embodiment, the kit includes a compound of Formula 1 in which F is $^{19}$F. In another embodiment, the compound is a compound of Formula 2. In another embodiment, the kit includes a compound of Formula 2 in which F is $^{19}$F. In another embodiment, the compound is a compound of Formula 3. In another embodiment, the kit includes a compound of Formula 3 in which F is $^{19}$F. In another embodiment, the compound is a compound of Formula 4. In another embodiment, the kit includes a compound of Formula 4 in which F is $^{19}$F. In another embodiment, the kit includes an $^{18}$F isotopic exchange reagent. In another embodiment, the kit includes an instruction manual for the use thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION OF ILLUSTRATIVE EMBODIMENTS

Figure 1:
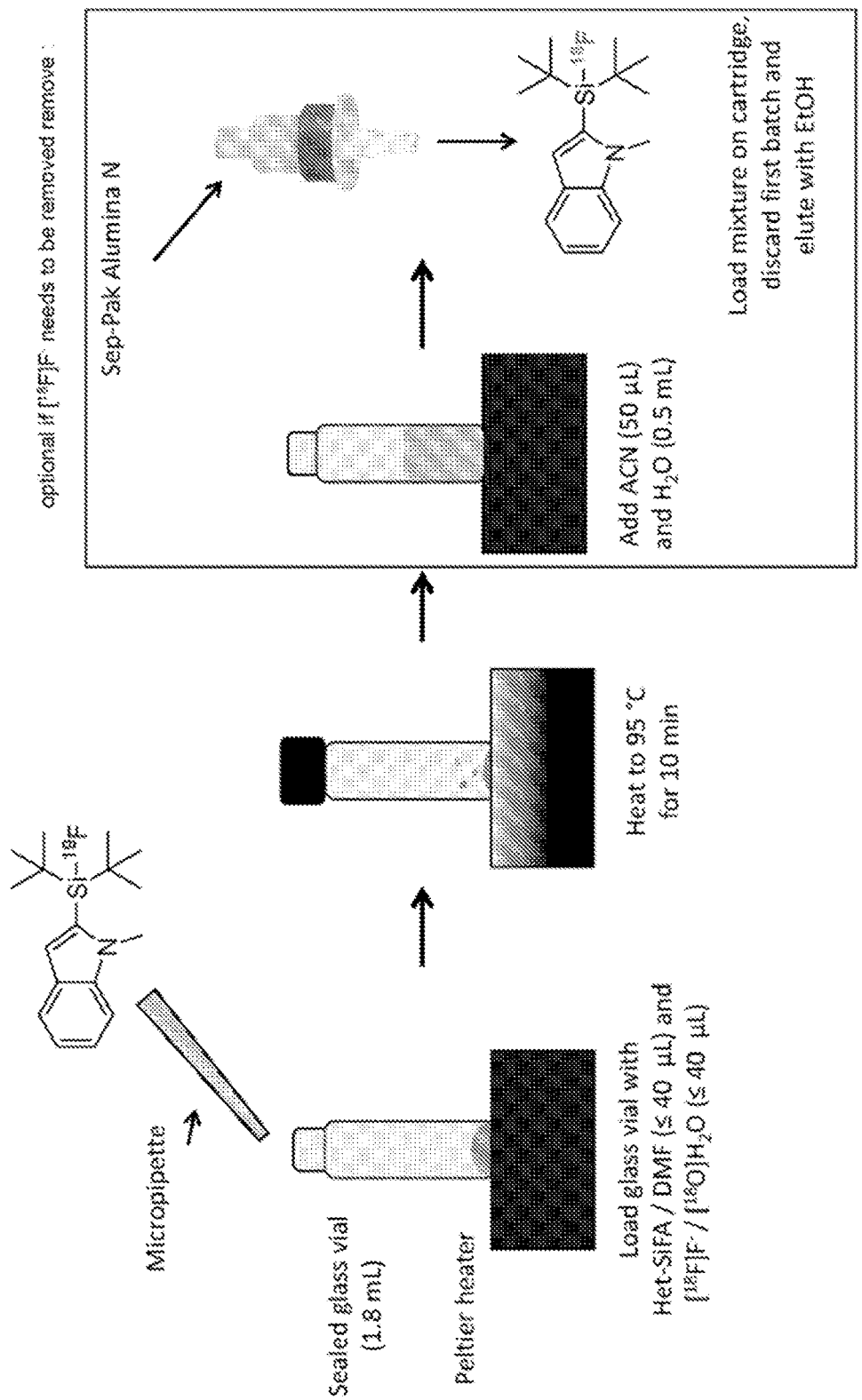
FIG. 1 is a schematic illustrating an exemplary process for $^{18}$F-labeling of an exemplary 1-methyl-indole heteroaromatic silicon-fluoride-acceptor.

The present invention relates to the unexpected discovery of novel heteroaromatic silicon-fluoride-acceptors useful for the $^{18}$F-radiolabeling of biomolecules. This novel class of heteroaromatic silicon-fluoride-acceptors significantly improves many aspects of currently available phenyl silicon-fluoride-acceptors in terms of their preparation and pharmacokinetic properties. As demonstrated herein, the synthesis of heteroaromatic silicon-fluoride-acceptors does not require the use of highly pyrophoric lithium or magnesium reagents, does not require pre-functionalization of the aryl, can potentially be scaled up to amounts that are of industrial interest, and uses cheaper and more environmentally friendly substrates which aligns with the current goals of sustainable chemistry. The huge variety of available heteroaromatic compounds that can be transformed into silicon-fluoride-acceptors enables the development of silicon-fluoride-acceptors with different electronic structures, polarities and free sites for derivatization, advantages which currently available phenyl silicon-fluoride-acceptors do not have. In one embodiment, the aromatic heterocycles included are derivatives of indole, 7-azaindole, benzothiophene, furan, pyrrole, pyrazole, imidazole and pyridine.

In one embodiment, the invention provides heteroaromatic silicon-fluoride-acceptors. In one embodiment, the invention provides $^{18}$F-labeled compounds derived from silicon-fluoride-acceptors.

In one embodiment, the precursors for silicon-fluoride-acceptors are synthetically accessible by a methodology using potassium tert-butoxide as a catalyst for the silylation of C—H bonds in aromatic heterocycles, methodology described by Toutov et al., Nature, 2015, 518:80-84, which is incorporated by reference herein in its entirety.

In one embodiment, the invention provides methods for $^{18}$F-radiolabeling of silicon-fluoride-acceptors by isotopic exchange. In one embodiment, the isotopic exchange is performed on various platforms including a commercial radiosynthesizer (ELYXIS, Sofie Biosciences), an in-house developed microfluidic Teflon®-coated chip, and a manual procedure in a sealed glass vial.

In one embodiment, the invention provides a kit for $^{18}$F-radiolabeling of silicon-fluoride-acceptors by isotopic exchange.

In one embodiment, the invention provides methods for $^{18}$F-based imaging methods, including, but not limited to, positron emission tomography (PET).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the terms "imaging agent," "imaging probe," or "imaging compound," means, unless otherwise stated, a molecule which can be detected by its emitted signal, such as positron emission, autofluorescence emission, or optical properties. The method of detection of the compounds may include, but are not necessarily limited to, nuclear scintigraphy, positron emission tomography (PET), single photon emission computed tomography (SPECT), magnetic resonance imaging, magnetic resonance spectroscopy, computed tomography, or a combination thereof depending on the intended use and the imaging methodology available to the medical or research personnel.

As used herein, the term "biomolecule" refers to any molecule produced by a living organism and may be selected from the group consisting of proteins, peptides, polysaccharides, carbohydrates, lipids, as well as analogs and fragments thereof. Preferred examples of biomolecules are proteins and peptides.

As used herein, the terms "bioconjugation" and "conjugation," unless otherwise stated, refers to the chemical derivatization of a macromolecule with another molecular entity. The molecular entity can be any molecule and can include a small molecule or another macromolecule. Examples of molecular entities include, but are not limited to, compounds of the invention, other macromolecules, polymers or resins, such as polyethylene glycol (PEG) or polystyrene, non-immunogenic high molecular weight compounds, fluorescent, chemiluminescent radioisotope and bioluminescent marker compounds, antibodies, biotin, diagnostic detector molecules, such as a maleimide derivatized fluorescein, coumarin, a metal chelator or any other modifying group. The terms bioconjugation and conjugation are used interchangeably throughout the Specification.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$OH, —CH$_2$—CH$_2$—NH—CH$_3$, —CH$_2$—S—CH$_2$—CH$_3$, and —CH$_2$—CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In one embodiment, the alkoxy group is (C$_1$-C$_3$) alkoxy, such as ethoxy and methoxy.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

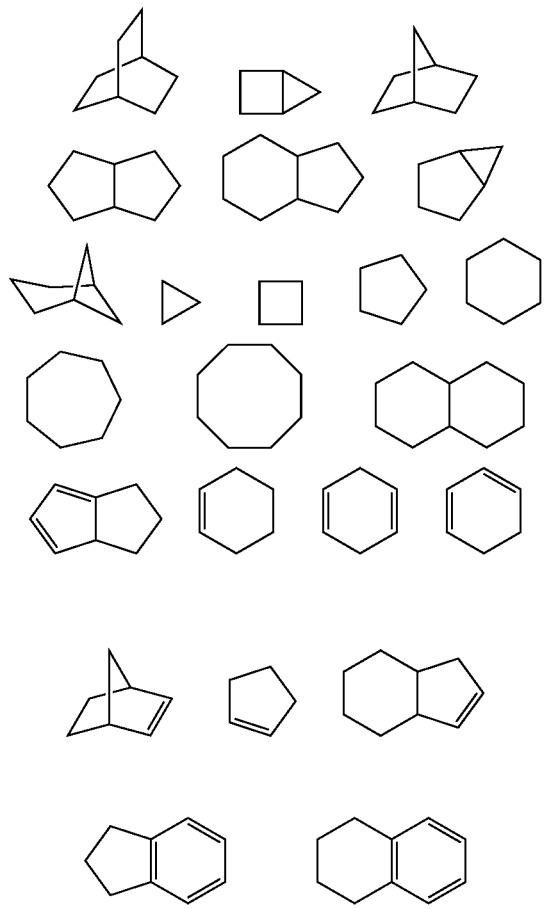

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon-carbon double bond or one carbon-carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

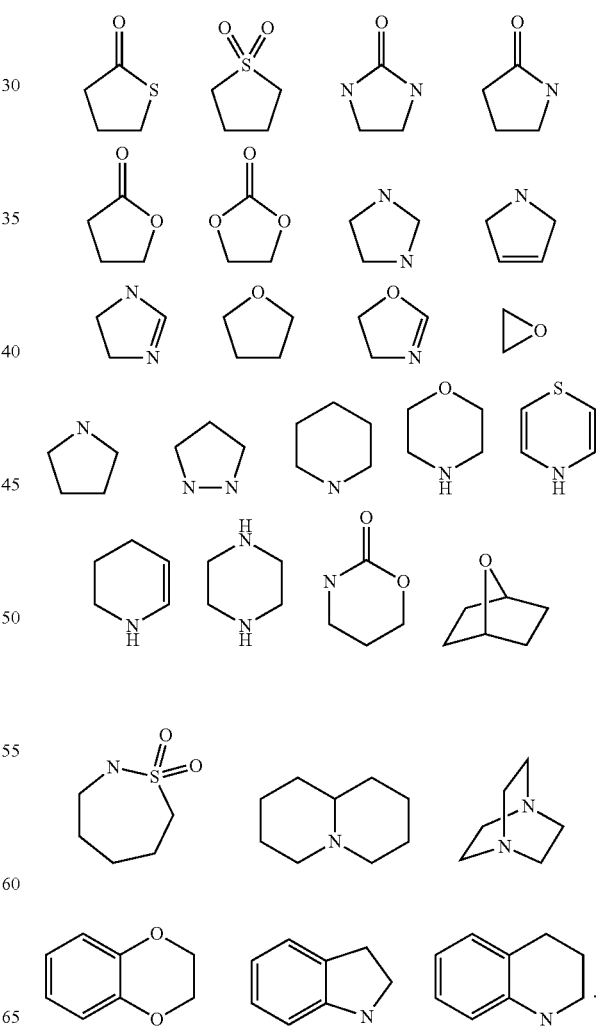

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π(pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. In one embodiment, the heteroaryl-($C_1$-$C_3$)alkyl is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. In one embodiment, the substituted heteroaryl-($C_1$-$C_3$)alkyl is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

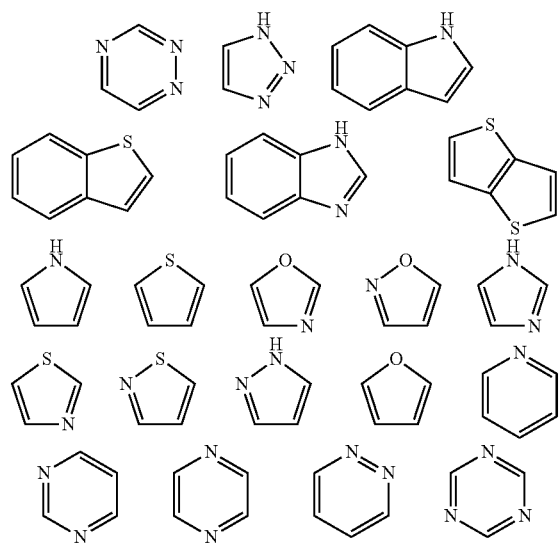

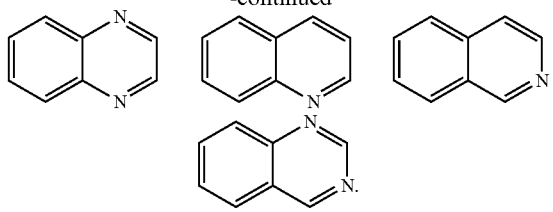

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —NH($CH_3$), —N($CH_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(═O)$_2$alkyl, —C(═O)NH[substituted or unsubstituted alkyl, or substituted or unsubstituted phenyl], —C(═O)N[H or alkyl]2, —OC(═O)N[substituted or unsubstituted alkyl]2, —NHC(═O)NH [substituted or unsubstituted alkyl, or substituted or unsubstituted phenyl], —NHC(═O)alkyl, —N[substituted or unsubstituted alkyl]C(═O)[substituted or unsubstituted alkyl], —NHC(═O)[substituted or unsubstituted alkyl], —C(OH)[substituted or unsubstituted alkyl]2, and —C(NH₂)[substituted or unsubstituted alkyl]2. In another embodiment, by way of example, an optional substituent is selected from oxo, fluorine, chlorine, bromine, iodine, —CN, —NH₂, —OH, —NH(CH₃), —N(CH₃)₂, —CH₃, —CH₂CH₃, —CH(CH₃)₂, —CF₃, —CH₂CF₃, —OCH₃, —OCH₂CH₃, —OCH(CH₃)₂, —OCF₃, —OCH₂CF₃, —S(=O)₂—CH₃, —C(=O)NH₂, —C(=O)—NHCH₃, —NHC(=O)NHCH₃, —C(=O)CH₃, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. In yet another heteroaromatic silicon-fluoride-acceptors exclusively improves many aspects of currently available phenyl silicon-fluoride-acceptors in terms of their preparation and pharmacokinetic properties. The huge variety of available heteroaromatic compounds that can be transformed into silicon-fluoride-acceptors enables the development of silicon-fluoride-acceptors with different electronic structures, polarities and free sites for derivatization, advantages which currently available phenyl silicon-fluoride-acceptors do not have. Table 1 highlights some of the unexpected improvements of exemplary compounds over a currently available silicon-fluoride-acceptors:

TABLE 1

| Existing state of the art phenyl silicon-fluoride-acceptor | Novel heteroaromatic silicon-fluoride-acceptor |
|---|---|
| 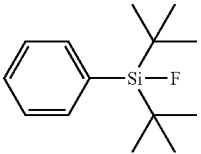 [SMILES: CC(C)(C)[Si](F)(c1ccccc1)C(C)(C)C] | 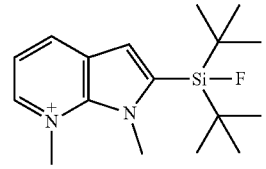 |
| Highly lipophilic (clogP = 4.47) | Moderately hydrophilic (clogP = −0.44) |
| Additional polar auxiliaries of high molecular weight (e.g. PEG-chains, polar groups, charges) are needed | Due to charged pyridine-moiety no or less additional polar auxiliaries are needed |
| No additional steric hindrance provided on phenyl | N-methyl group on pyrrole-moiety additionally increases steric hindrance |
| Phenyl moiety weakly decreases Lewis acidity on silicon | Electron rich pyrrole moiety strongly decreases Lewis acidity on silicon | embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

DESCRIPTION

The present invention relates to the unexpected discovery of novel heteroaromatic silicon-fluoride-acceptors useful for the ¹⁸F-radiolabeling of biomolecules. This novel class of Compounds The compounds of the present invention may be synthesized using techniques well-known in the art of organic synthesis. The starting materials and intermediates required for the synthesis may be obtained from commercial sources or synthesized according to methods known to those skilled in the art.

In one aspect, the invention provides a compound of Formula 1:

Formula 1 wherein in Formula 1,

F is selected from the group consisting of ¹⁹F and ¹⁸F;

$A^1$ is a monocyclic or bicyclic heteroaryl ring optionally substituted with 0-4 $R^a$ groups;

$R^a$ is selected, at each independent occurrence, from the group consisting of null, H, F, Cl, Br, I, CN, NO₂, OR$^c$, OC(=O)R$^c$, OC(=O)OR$^c$, OC(=O)NR$^c$R$^d$, CR$^c$R$^d$, COR$^c$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)₂R$^d$, NR$^c$S(=O)₂NR$^d$R$^e$, SR$^c$, S(=O)R$^c$, S(=O)₂R$^c$, and S(=O)₂NR$^c$R$^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^c$, OC(=O)R$^c$, OC(=O)OR$^c$, OC(=O)NR$^c$R$^d$, CR$^c$R$^d$, COR$^c$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)$_2$R$^d$, NR$^c$S(=O)$_2$NR$^d$R$^e$, SR$^c$, S(=O)R$^c$, S(=O)$_2$R$^c$, and S(=O)$_2$NR$^c$R$^d$, or independent R$^a$ groups can optionally be joined to form additional rings;

R$^c$, R$^d$ and R$^e$ are selected, at each independent occurrence, from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and any of R$^c$, R$^d$ or R$^e$ can optionally be joined to form additional rings; and R$^1$ and R$^2$ are each independently an alkyl group.

In another aspect, the invention provides a compound of Formula 2:

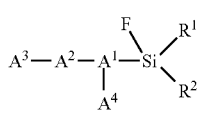

Formula 2 wherein in Formula 2,
F is selected from the group consisting of $^{19}$F and $^{18}$F;
A$^1$ is a monocyclic or bicyclic heteroaryl ring optionally substituted with 0-4 R$^a$ groups;
A$^2$ is a linker;
A$^3$ is a moiety capable of chemical conjugation or bioconjugation;
A$^4$ is a moiety comprising a polar auxiliary that may optionally contain a charge;
R$^a$ is selected, at each independent occurrence, from the group consisting of null, H, F, Cl, Br, I, CN, NO$_2$, OR$^c$, OC(=O)R$^c$, OC(=O)OR$^c$, OC(=O)NR$^c$R$^d$, CR$^c$R$^d$, COR$^c$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)$_2$R$^d$, NR$^c$S(=O)$_2$NR$^d$R$^e$, SR$^c$, S(=O)R$^c$, S(=O)$_2$R$^c$, and S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^c$, OC(=O)R$^c$, OC(=O)OR$^c$, OC(=O)NR$^c$R$^d$, CR$^c$R$^d$, COR$^c$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)$_2$R$^d$, NR$^c$S(=O)$_2$NR$^d$R$^e$, SR$^c$, S(=O)R$^c$, S(=O)$_2$R$^c$, and S(=O)$_2$NR$^c$R$^d$, or independent R$^a$ groups can optionally be joined to form additional rings;

R$^c$, R$^d$ and R$^e$ are selected, at each independent occurrence, from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and any of R$^c$, R$^d$ or R$^e$ can optionally be joined to form additional rings; and R$^1$ and R$^2$ are each independently an alkyl group.

In another aspect, the invention provides a compound of Formula 3:

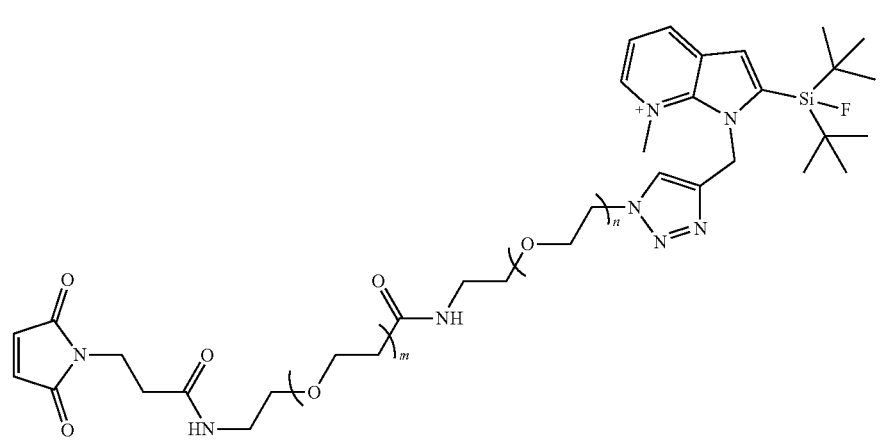

Formula 3 wherein in Formula 3,
F is selected from the group consisting of $^{19}$F and $^{18}$F; and
m and n are each independently an integer selected from the group consisting of 0, 1, 2, 3, 4, 5, and 6.

In another aspect, the invention provides a compound of Formula 4:

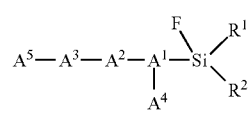

Formula 4 wherein in Formula 4,
F is selected from the group consisting of $^{19}$F and $^{18}$F;
A$^1$ is a monocyclic or bicyclic heteroaryl ring optionally substituted with 0-4 R$^a$ groups;
A$^2$ is a linker;
A$^3$ is a moiety capable of chemical conjugation or bioconjugation;

A⁴ is a moiety comprising a polar auxiliary that may optionally contain a charge;

A⁵ is a moiety comprising a disease targeting molecule or biomolecule;

$R^a$ is selected, at each independent occurrence, from the group consisting of null, H, F, Cl, Br, I, CN, NO₂, OR$^c$, OC(=O)R$^c$, OC(=O)OR$^c$, OC(=O)NR$^c$R$^d$, CR$^c$R$^d$, COR$^c$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)₂R$^d$, NR$^c$S(=O)₂NR$^d$R$^e$, SR$^c$, S(=O)R$^c$, S(=O)₂R$^c$, and S(=O)₂NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO₂, OR$^c$, OC(=O)R$^c$, OC(=O)OR$^c$, OC(=O)NR$^c$R$^d$, CR$^c$R$^d$, COR$^c$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)₂R$^d$, NR$^c$S(=O)₂NR$^d$R$^e$, SR$^c$, S(=O)R$^c$, S(=O)₂R$^c$, and S(=O)₂NR$^c$R$^d$, or independent $R^a$ groups can optionally be joined to form additional rings;

$R^c$, $R^d$ and $R^e$ are selected, at each independent occurrence, from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and any of $R^c$, $R^d$ or $R^e$ can optionally be joined to form additional rings; and $R^1$ and $R^2$ are each independently an alkyl group.

In one embodiment, the heteroaromatic ring A¹ is selected from the group consisting of indole, azaindole, 7-azaindole, benzothiophene, furan, pyrrole, pyrazole, imidazole, and pyridine. In one embodiment, R¹ and R² each independently selected from the group consisting of methyl, ethyl, propyl, isopropyl, and tert-butyl. In one embodiment, R¹ and R² are tert-butyl groups. In one embodiment, the heteroaromatic ring A¹ is selected from the group consisting of indole, 7-azaindole, benzothiophene, furan, pyrrole, pyrazole, imidazole, and pyridine, and R¹ and R² are tert-butyl groups. In one embodiment, the linker A² includes an unsubstituted alkyl. In one embodiment, the linker A² includes an unsubstituted polyethylene glycol (PEG). In one embodiment, the linker A² includes a PEG4 linker. In one embodiment, the linker A² includes a PEG6 linker. In one embodiment, the linker A² includes a disubstituted triazole. In one embodiment, A³ is selected from the group consisting of an activated ester such as succinimide, an N-hydroxysuccinimide (NHS) ester, a maleimide, an amide, and a maleimide-thiol adduct. In one embodiment, a PEG-spacer is added for additional polarity. In one embodiment, A⁴ is a carboxylic acid. In one embodiment, A⁵ is an engineered antibody fragment. In one embodiment, A⁵ is an anti-PSCA A2 cys-diabody.

Exemplary embodiments of the heteroaromatic silicon-fluoride-acceptors of the invention are highlighted in Tables 2 and 3 (the name indicates the corresponding heteroaromatic ring, and the substitution site indicates, without limitation, potential connectivity sites for a linker, and/or any other ancillary group):

TABLE 2

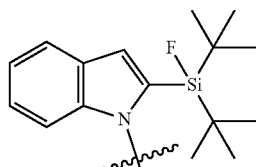

indole

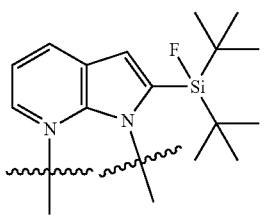

7-azaindole

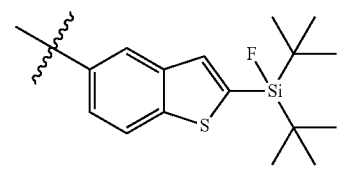 [SMILES: *c1ccc2sc([Si](F)(C(C)(C)C)C(C)(C)C)cc2c1]

benzothiophene

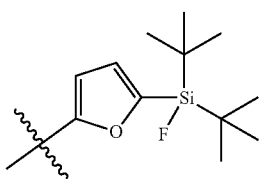 [SMILES: *c1ccc([Si](F)(C(C)(C)C)C(C)(C)C)o1]

furan

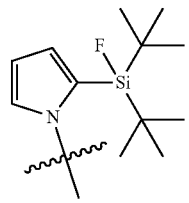 [SMILES: *n1cccc1[Si](F)(C(C)(C)C)C(C)(C)C]

pyrrole

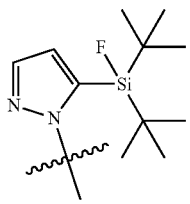 [SMILES: *n1nccc1[Si](F)(C(C)(C)C)C(C)(C)C]

pyrazole

TABLE 2-continued

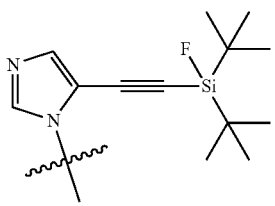 [SMILES: *n1cncc1C#C[Si](F)(C(C)(C)C)C(C)(C)C]

imidazole

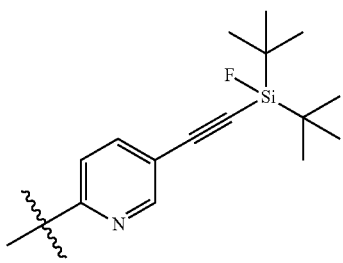 [SMILES: *c1ccc(C#C[Si](F)(C(C)(C)C)C(C)(C)C)cn1]

pyridine

TABLE 3

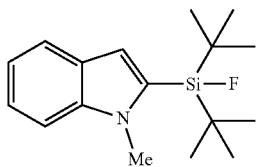 [SMILES: Cn1c([Si](F)(C(C)(C)C)C(C)(C)C)cc2ccccc21]

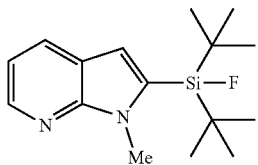 [SMILES: Cn1c([Si](F)(C(C)(C)C)C(C)(C)C)cc2cccnc21]

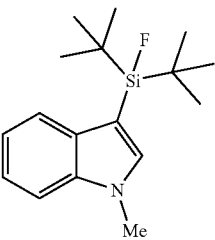 [SMILES: Cn1cc([Si](F)(C(C)(C)C)C(C)(C)C)c2ccccc21]

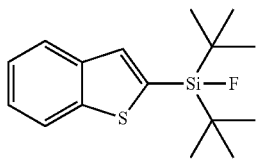 [SMILES: CC(C)(C)[Si](F)(c1cc2ccccc2s1)C(C)(C)C]

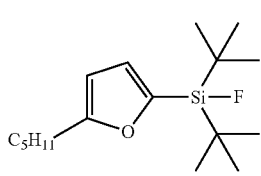

TABLE 3-continued

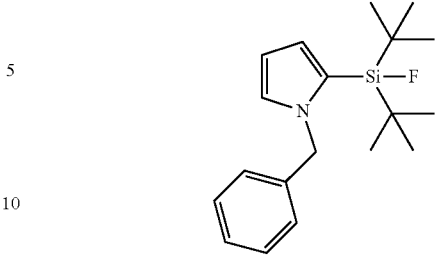

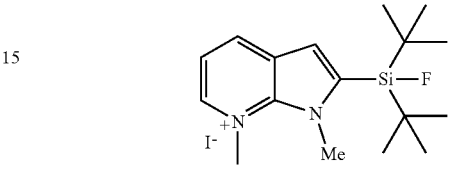

Preparation of the Compounds of the Invention

Compounds of Formulae 1, 2, 3, and 4 may be prepared by the general schemes described herein, using synthetic methods known by those skilled in the art. The following examples illustrate non-limiting embodiments of the invention.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, sites on, for example, the heteroaromatic or aromatic ring portion of compounds of the invention are susceptible to various metabolic reactions. Incorporation of appropriate substituents on the heteroaromatic or aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

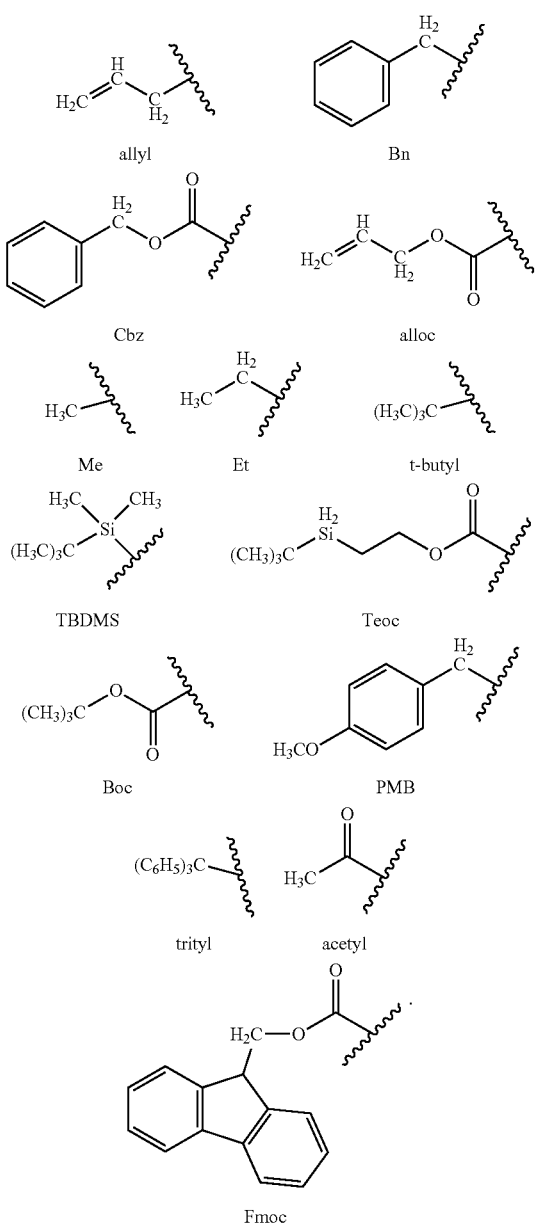

Other protecting groups, plus a detailed description of techniques applicable to the creation of protecting groups and their removal are described in Greene & Wuts, Protective Groups in Organic Synthesis, 3rd Ed., John Wiley &

Sons, New York, NY, 1999 ("Greene"), and Kocienski, Protective Groups, Thieme Verlag, New York, NY, 1994, which are incorporated herein by reference for such disclosure.

Such groups for use in protecting amine N—H bonds (i.e., amine protecting groups, including those of imidazoles, pyrroles, and indoles), as set forth in Greene, include:

sulfonyls such as methanesulfonyl (Ms), trifluoromethanesulfonyl, 2-(trimethyl silyl)ethanesulfonyl, N,N-dimethylsulfamoyl, mesitylenesulfonyl, p-methoxyphenyl sulfonyl (Mps), benzenesulfonyl (B s), benzenesulfenyl, p-toluenesulfonyl (tosyl), 2,4,6-trimethylbenzenesulfonyl, trifluoromethylsulfonyl, phenacylsulfonyl, 2,3,6-trimethyl-4-methoxybenzenesulfonyl (Mtr), 2,4,6-trimethoxybenzenesulfonyl (Mtb), 2,6-dimethyl-4-methoxybenzenesulfonyl (Mds), pentamethylbenzenesulfonyl (Pme), 2,3,5,6-tetramethyl-4-methoxybenzenesulfonyl (Mte), 4-methoxybenzenesulfonyl (Mbs), 2,6-dimethoxy-4-methylbenzenesulfonyl (iMds), 3-methoxy-4-t-butylbenzenesulfonyl, 2,4-dinitrobenzenesulfonyl (DNs), or pyridine-2-sulfonyl;

alkoxycarbonyls and aryloxycarbonyls (forming carbamates) such as 9-fluorenylmethoxycarbonyl (Fmoc), 9-(2-sulfo)fluorenylmethoxycarbonyl, 9-(2,7-dibromo)fluorenylmethoxycarbonyl, 17-tetrabenzo[a,c,g,i]fluorenylmethoxycarbonyl (Tbfmoc), 2-chloro-3-indenylmethyloxy arbonyl (Climoc), benz[f]linden-3-ylmethoxycarbonyl (Bimoc), 2,7-di-t-butyl[9-(10,10-dioxo-10,10,10,10-tetrahydrothioxanthyl)] methoxycarbonyl (DBD-Tmoc), 1,1-dioxobenzo[b]thiophene-2-ylmethoxycarbonyl (Bimoc), methoxycarbonyl, 9-fluorenylmethoxycarbonyl, 2,2,2-trichloroethoxycarbonyl (Troc), 2-(trimethylsilyl)ethoxycarbonyl (Teoc), t-butoxycarbonyl (BOC), cyclobutoxycarbonyl, 2,4-dimethylpent-3-lyoxycarbonyl (Doc), cyclohexyloxycarbonyl (Hoc), 1,1-dimethyl-2,2,2-trichloroethoxycarbonyl (TcBOC), 1,1-dimethyl-2-haloethoxycarbonyl, 1,1-dimethyl-2-cyanoethoxycarbonyl, 1-adamantyloxycarbonyl (1-Adoc), 2-adamantyloxycarbonyl (2-Adoc), allyloxycarbonyl (Aloc), 1-isopropylallyloxycarbonyl (Ipaoc), vinyloxycarbonyl (Voc), cinnamyloxycarbonyl (CoC), 4-nitrocinnamyloxycarbonyl (Noc), 3-(3'-pyridyl)prop-2-enyloxycarbonyl (Paloc), 8-quinolyloxycarbonyl, alkyldithiocarbonyl, benzyloxycarbonyl (Cbz), p-methoxybenzyloxycarbonyl (Moz), p-nitrobenzyloxycarbonyl (PNZ), p-bromobenzyloxycarbonyl, p-chlorobenzyloxycarbonyl, 3,4-dimethoxybenzyloxycarbonyl, 2,4-dichlorobenzyloxycarbonyl, 4-methyl sulfinylbenzyloxycarbonyl (Msz), 9-anthrylmethoxycarbonyl, diphenylmethoxycarbonyl, 2-methylthioethoxycarbonyl, 2-methylsulfonylethoxycarbonyl, 2-(p-toluenesulfonyl)ethoxycarbonyl, 4-methylthiophenoxycarbonyl (Mtpc), 1,1-dimethyl-2cyanoethoxy carbonyl, 2-dansylethoxycarbonyl (Dnseoc), 2-(4-nitrophenyl)ethoxycarbonyl (Npeoc), 4-phenylacetoxybenzyloxy carbonyl (PhAcOZ), m-chloro-p-acyloxybenzyloxycarbonyl, p-(dihydroxyvoryl)benzyloxycarbonyl (Dobz), 5-benzisoxazolylmethoxycarbonyl (Bic), 2-(trifluoromethyl)-6-chromonylmethyleneoxycarb onyl (Tcroc), 2-phenylethyloxycarbonyl (hZ), 1-methyl-1-phenylethyloxycarbonyl, 1-(1-adamantyl)-1-methylethoxy carbonyl (Adpoc), 2-chloroethoxycarbonyl, 1,1-dimethyl-2-haloethoxycarb onyl, 1,1-dimethyl-2,2-dibromomethoxycarbonyl (DB-t-BOC), 1-methyl-1-(4-biphenyl)ethoxycarbonyl (Bpoc), 1-(3,5-di-t-butylphenyl)1-methylethoxycarbonyl (t-Bumeoc), 2-(2'-pyridyl)ethoxycarbonyl (Pyoc), 2-(4'-pyridyl)ethoxycarbonyl (Pyoc), 2,2-bis(4'-nitrophenyl)ethoxycarbonyl (Bnpeoc), N-(2-pivaloylamino)-1,1-dimethylethoxycarbonyl, or 2-(N,N-dicyclohexylcarboxamido) entyloxycarbonyl;

alkyls and aryls such as methyl, benzenyloxymethyl, pivoyloxymethyl, di-(p-methoxyphenyl)methyl, triphenylmethyl (Tr), (4-methoxyphenyl)diphenylmethyl (MMTr), t-butyl, cyanomethyl, 2,4-dimethoxybenzyl (Dmb), vinyl, 2-chloroethyl, (1-ethoxy)ethyl (EE), 2-(2'-pyridyl)ethyl), 2-(4'-pyridyl)ethyl), 2-(4-nitrophenyl)ethyl (PNPE), 2,4-dinitrophenyl, allyl, benzyl (Bn), o-nitrobenzyl, 2-hydroxybenzyl (HBn), p-methoxybenzyl (MPM), 2,4-dimethoxybenzyl (DMPM), 3,4-dimethoxybenzyl, 3-methoxybenzyl, 3,5-dimethoxybenzyl, 2-nitrobenzyl, 2,4-dinitrophenyl, phenacyl, triphenylmethyl (Tr), diphenylmethyl (Dpm), diphenyl-4-pyridylmethyl (Dppm), hydroxymethyl, methoxymethyl (MOM), diethoxymethyl (DEM), 2-chloroethoxymethyl, 2-(trimethylsilyl)ethoxymethyl (SEM), t-butoxymethyl (BUM), t-butyldimethylsiloxymethyl, pivaloyloxymethyl (POM), benzyloxymethyl (BOM), dimethylaminomethyl, 2-tetrahydropyranyl (THP), or acetoxypropyl;

formyl, alkylcarbonyls, and arylcarbonyls such as acetyl, acetoacetyl, N,N-diethylaminocarbonyl, chloroacetyl, dichloroacetyl, trichloroacetyl, trifluoroacetyl, phenylacetyl, phenacyl, o-nitrophenylacetyl, o-nitrophenoxyacetyl, t-butylcarbonyl, 3-phenylpropionoyl, 3-(p-hydroxyphenyl)propionyl, 2-methyl-2-(o-nitrophenoxy) propionyl, 2-methyl-2-(o-phenylazophenoxy) propionyl, 4-chlorobutyryl, 4-pentenoyl, picolinoyl, benzoylphenylalanyl, benzoyl, p-phenylbenzoyl, or phthaloyl; and trialkyl/aryl silyl as trimethylsilyl, triethylsilyl, triisopropylsilyl, dimethylisopropylsilyl (IPDMS), diethylisopropylsilyl (DEIPS), dimethylthexylsilyl (TDS), t-butyldimethylsilyl (TBDMS), t-butyldiphenylsilyl (TBDPS), tribenzylsilyl, triphenylsilyl (TPS), or tri-p-xylylsilyl diphenylmethylsilyl (DPMS)di-t-butylmethylsilyl (DTBMS).

In one embodiment, the invention provides a method of synthesis of heteroaromatic Silicon-Fluoride Acceptors (Si-FAs). In one embodiment, the precursors for silicon-fluoride-acceptors are synthetically accessible by a methodology using potassium tert-butoxide as a catalyst for the silylation of C—H bonds in aromatic heterocycles, methodology described by Toutov et al., Nature, 2015, 518:80-84, which is incorporated herein in its entirety.

Scheme 1 depicts an exemplary method for the synthesis of silicon-fluoride-acceptors. Accordingly, a heteroaromatic compound can be first treated with a catalytic amount of potassium tert-butoxide, and then reacted with di-tert-butyl silane, to afford an intermediate heteroarylsilane. The intermediate is thereafter reacted with potassium fluoride in the presence of a crown ether, to afford a $^{19}$F-silicon-fluoride-acceptors compound of the current invention.

Scheme 1

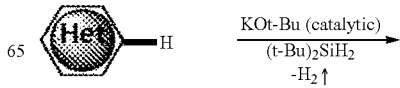

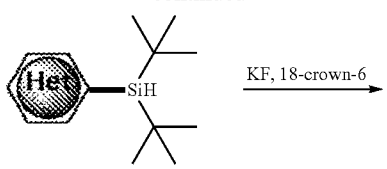

KF, 18-crown-6

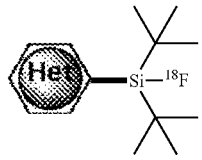

Compounds described herein include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O, $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed. In one embodiment, the compounds described herein are labeled by other means, including, but not limited to, the use of chromophores or fluorescent moieties, bioluminescent labels, or chemiluminescent labels.

In one embodiment, the invention provides methods for $^{18}$F-radiolabeling of silicon-fluoride-acceptors by isotopic exchange. The novel class of heteroaromatic silicon-fluoride-acceptors described herein can be labeled with the PET isotope $^{18}$F on various platforms. In one embodiment, the isotopic exchange is performed on various platforms including a commercial radiosynthesizer (ELYXIS, Sofie Biosciences), an in-house developed microfluidic Teflon®-coated chip, and a manual procedure in a sealed glass vial.

Scheme 2 depicts an exemplary method of performing the $^{19}$F to $^{18}$F isotopic exchange. Accordingly, a $^{19}$F-silicon-fluoride-acceptors compound of the current invention can be exchanged with an $^{18}$F-fluoride, to afford an $^{18}$F-compound of the current invention.

Scheme 2

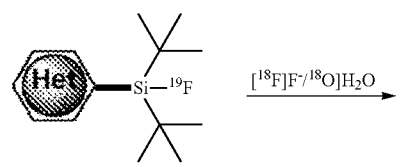

[$^{18}$F]F$^-$/$^{18}$O]H$_2$O

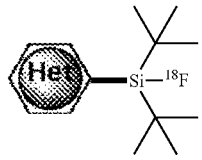

Purification of the labeled compound can be performed using any method known in the art. In a non-limiting example, purification of the final labeling product is achieved by a cartridge purification ($C_{18}$ or alumina).

Kits of the Invention

The present invention encompasses various kits for $^{18}$F-labeling of heteroaromatic silicon-fluoride-acceptors, the kit comprising a heteroaromatic silicon-fluoride-acceptor, an $^{18}$F-labeling reagent, and an instructional materials which describe use of the kit to perform the methods of the invention. These instructions simply embody the methods and examples provided herein. Although model kits are described below, the contents of other useful kits will be apparent to the skilled artisan in light of the present disclosure. Each of these kits is contemplated within the present invention. A kit is envisaged for each embodiment of the present invention.

The heteroaromatic silicon-fluoride-acceptors of the present kit essentially includes the elements disclosed elsewhere herein. The heteroaromatic silicon-fluoride-acceptor can comprise a monocyclic or bicyclic heteroaryl ring optionally substituted, a linker, a moiety capable of chemical conjugation or bioconjugation, a moiety comprising a polar auxiliary that may optionally contain a charge, and a moiety comprising a disease targeting molecule or biomolecule. The $^{18}$F-labeling reagent can comprise [$^{18}$F]F$^-$ from the cyclotron.

The kits of the present invention can further comprise additional reagents disclosed herein, such as plates and dishes used in the methods of the present invention, buffers, solutions and the like, as well as an applicator or other implements for performing the methods of the present invention. The kits of the present invention further comprise an instructional material. In one embodiment the kit comprises micropipettes, vials, a Teflon®-coated glass chip, a heater, and an alumina or other suitable purification cartridge.

Those skilled in the art recognize or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Example 1: Manual $^{18}F$ Labeling of a Silicon-Fluoride-Acceptor in a Sealed Vial without Adding a Phase Transfer Catalyst or Preceding $^{18}F$ Activation

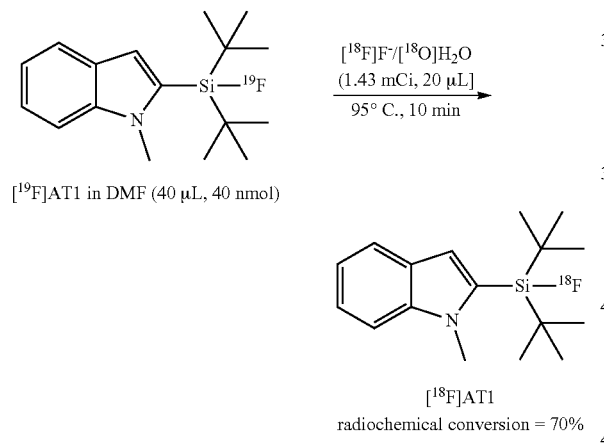

The exemplary compound 1-methyl-indole-silicon-fluoride-acceptors was labeled in a simple and fast radiosynthesis using wet $[^{18}F]F^-$ from the cyclotron. Unreacted $[^{18}F]F^-$ was efficiently removed with a Sep-Pak Alumina N cartridge. This method is also the basis for a preparation kit. An example of this method is also depicted in FIG. 1. Batch results are summarized in Table 4.

Example 2: $^{18}F$ Labeling of a Silicon-Fluoride-Acceptor on a Commercial Radiosynthesizer (ELYXIS, Sofie Biosciences)

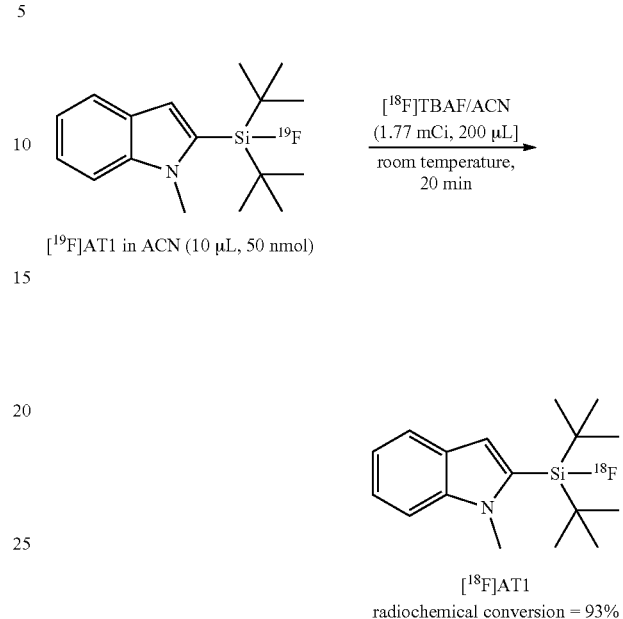

Exemplary compound 1-Methyl-indole-silicon-fluoride-acceptor was labeled with $[^{18}F]TBAF$ in ACN, using a commercial radiosynthesizer (ELYXIS, Sofie Biosciences).

Example 3: One-Step-Labeling on a Batch Microfluidic Device: $^{18}F$ Labeling of a Silicon-Fluoride-Acceptor on a Microfluidic Teflon®-Coated Chip in a True One-Step Radiochemical Reaction Under Mild Conditions Starting with Cyclotron Derived $[^{18}F]$Fluoride in $[^{18}O]H_2O$

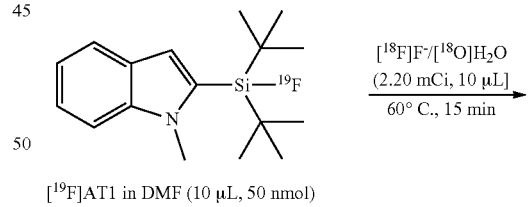

TABLE 4

| Heteroaromatic silicon-fluoride-acceptors | RCC | RCY (d.c.) | Time | RCP | SA ($A_S$) |
|---|---|---|---|---|---|
| 40 nmol | (61 ± 13)% (n = 4) | (32 ± 8)% (n = 2) | (25 ± 4) min (n = 2) | >99% | 30-31 mCi/μmol |
| 20 nmol | (44 ± 16)% (n = 2) | 28-XX % (n = 2) | 24-XX min (n = 2) | >99% | 44 mCi/μmol |
| 40 nmol | (59 ± 12)% (n = 5) | (42 ± 19)% (n = 3) | (24 ± 3) min (n = 3) | >99% | 28-31 mCi/μmol |
| 20 nmol | (46 ± 15)% (n = 4) | (31 ± 20)% (n = 3) | (23 ± 1) min (n = 3) | >99% | 44-72 mCi/μmol |

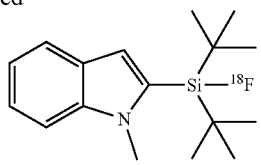

[18F]AT1
radiochemical conversion = 93%

Figure 2:
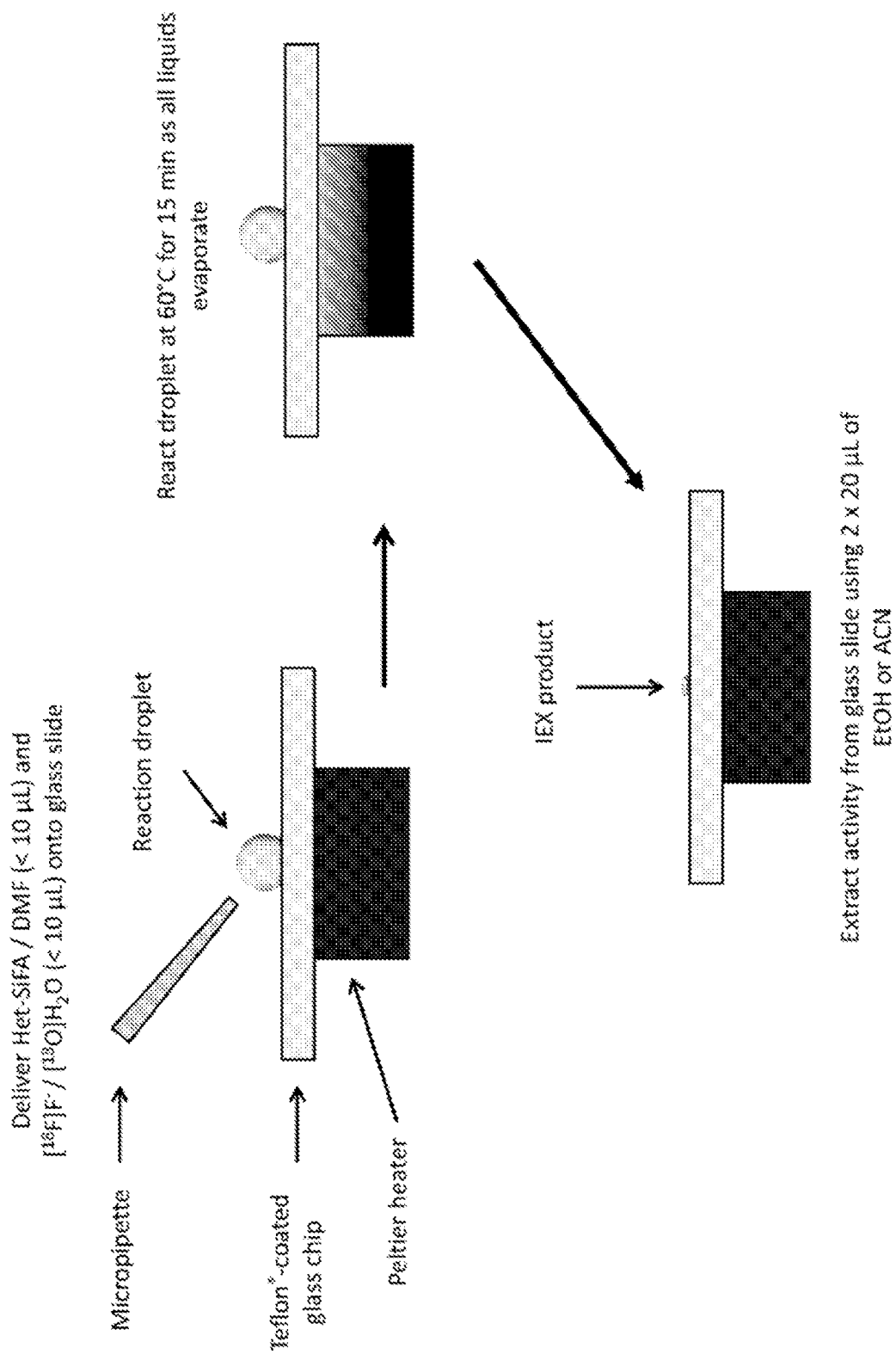
FIG. 2 is a schematic illustrating an exemplary one-step $^{18}$F labeling process of 1-methyl-indole-silicon-fluoride-acceptors on a microfluidic device.

Exemplary compound 1-Methyl-indole-silicon-fluoride-acceptor was labeled with aqueous [$^{18}$F]F$^-$ using a Teflon®-coated glass chip on a thermoelectric heater. FIG. 2 is a further graphical depiction of the process of $^{18}$F labeling of a silicon-fluoride-acceptor on a microfluidic Teflon® coated chip in a true one-step radiochemical reaction under mild conditions starting with cyclotron derived [$^{18}$F]fluoride in [$^{18}$O]1-120. Batch results are summarized in Table 5.

TABLE 5

| Heteroaromatic silicon-fluoride-acceptors | F$^-$ | Solvent | Additive | Temp | Min | RCC |
|---|---|---|---|---|---|---|
| 50 nmol | aq. [$^{18}$F]F$^-$ | ACN | — | 60° C. | 15 | 2% |
| 50 nmol | aq. [$^{18}$F]F$^-$ | DMSO | — | 60-80° C. | 35 | 19% |
| 5 nmol | aq. [$^{18}$F]F$^-$ | DMF | Thexyl alcohol | 60° C. | 12 | 12% |
| 10 nmol | aq. [$^{18}$F]F$^-$ | DMF | TBACO$_3$ | 60° C. | 14 | 0% |
| 50 nmol | aq. [$^{18}$F]F$^-$ | DMF | — | 60° C. | 15 | 86-93% |
| 10 nmol | aq. [$^{18}$F]F$^-$ | DMF | — | 60° C. | 15 | 64-66% |
| 5 nmol | aq. [$^{18}$F]F$^-$ | DMF | — | 60° C. | 13 | 28-44% |
| 100 nmol | aq. [$^{18}$F]TBAF* | ACN | — | rt | 10 | 85% |
| 5 nmol | aq. [$^{18}$F]TBAF* | ACN | — | rt | 10 | 42% |

*Obtained on the chip by azeotropic drying of [$^{18}$F]F$^-$/[$^{18}$O]H$_2$O in the presence of TBACO$_3$ and ACN.

Example 4: Kinetic Study

Figure 3:
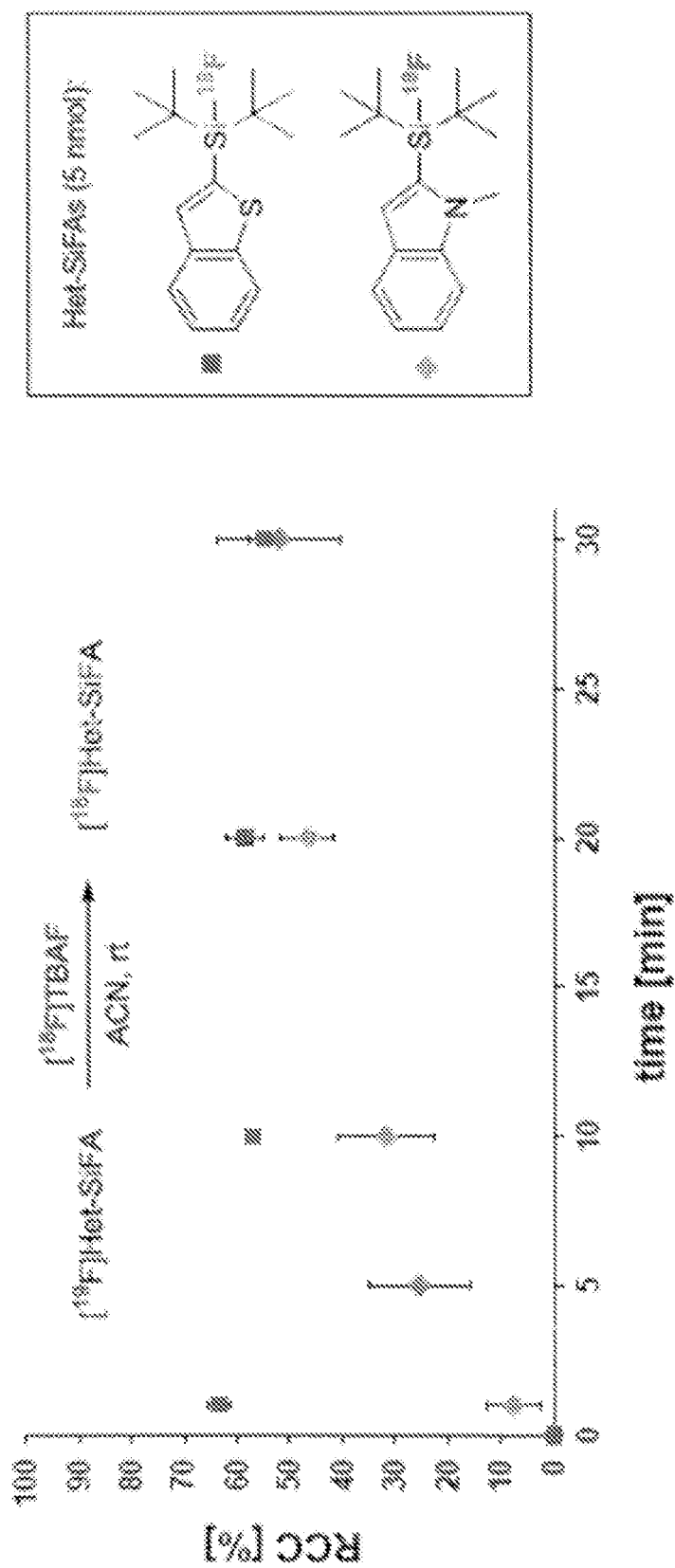
FIG. 3 is a graph depicting the results of a kinetic study on RCCs over time in the IEX of an exemplary benzothiophene-silicon-fluoride-acceptors and an exemplary 1-methyl-indole-silicon-fluoride-acceptors with chip-produced [$^{18}$F]TBAF (tetra-n-butylammonium fluoride).
Figure 4:
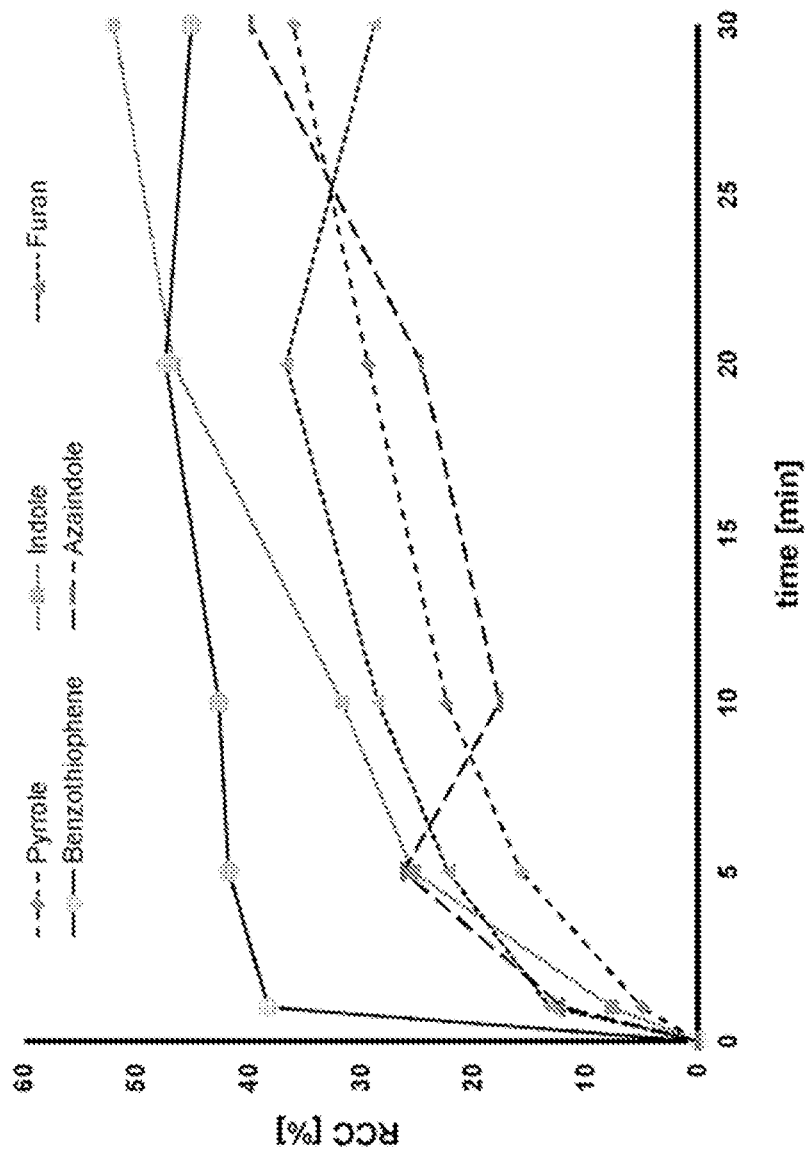
FIG. 4 is a graph depicting the results of a kinetic study on RCCs over time in the IEX of several different heteroaromatic silicon-fluoride-acceptors.

The RCCs over time in the IEX of various different heteroaromatic silicon-fluoride-acceptors were determined (FIGS. 3 and 4). The significant varieties in the [$^{18}$F]F$^-$ incorporation rates demonstrate differences in the electronic and structural parameters of the compounds.

Example 5: Heteroaromatic Silicon-Fluoride-Acceptor for Further Functionalization

TABLE 6 heteroaromatic silicon-fluoride-acceptors for bioorthogonal conjugation to biomolecules clickable — fast labeling clickable — improved stability Novel 18F-heteroaromatic silicon-fluoride-acceptor-TCO (trans cyclooctene)

Example 6: Alkyne-Silicon-Fluoride-Acceptors
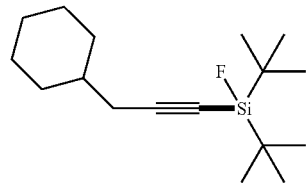
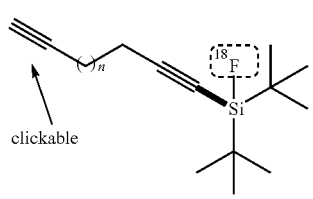
clickable
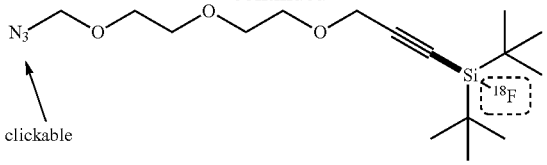
clickable
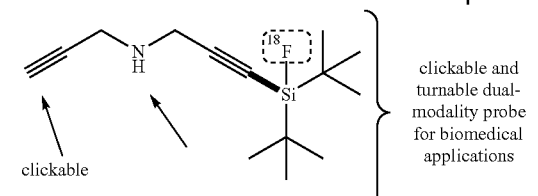
clickable and tunable dual-modality probe for biomedical applications
alkylate with fluorescent probe or other modality
Example 7: TCO-Silicon-Fluoride-Acceptor as a Prosthetic Group for Kit-Like Protein Labeling
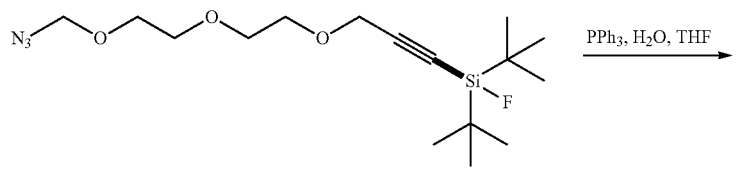
N3-PEG3-alkyne-SiFA
clogP = 3.35
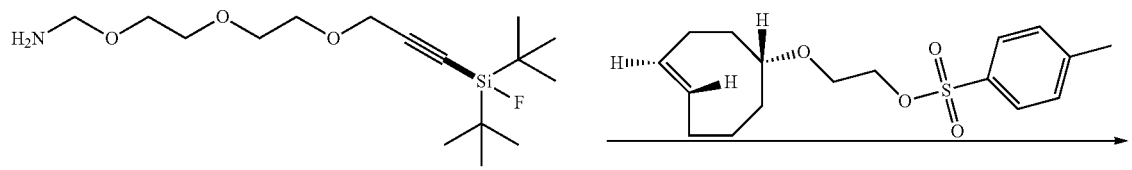
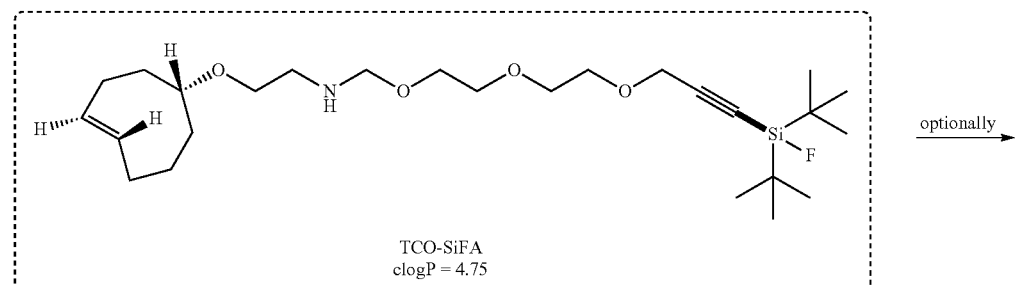
TCO-SiFA
clogP = 4.75
optionally
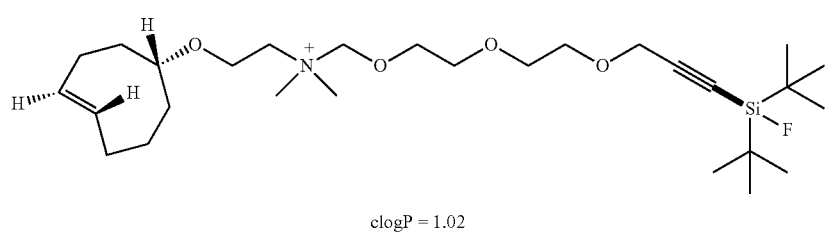
clogP = 1.02

Figure 5:
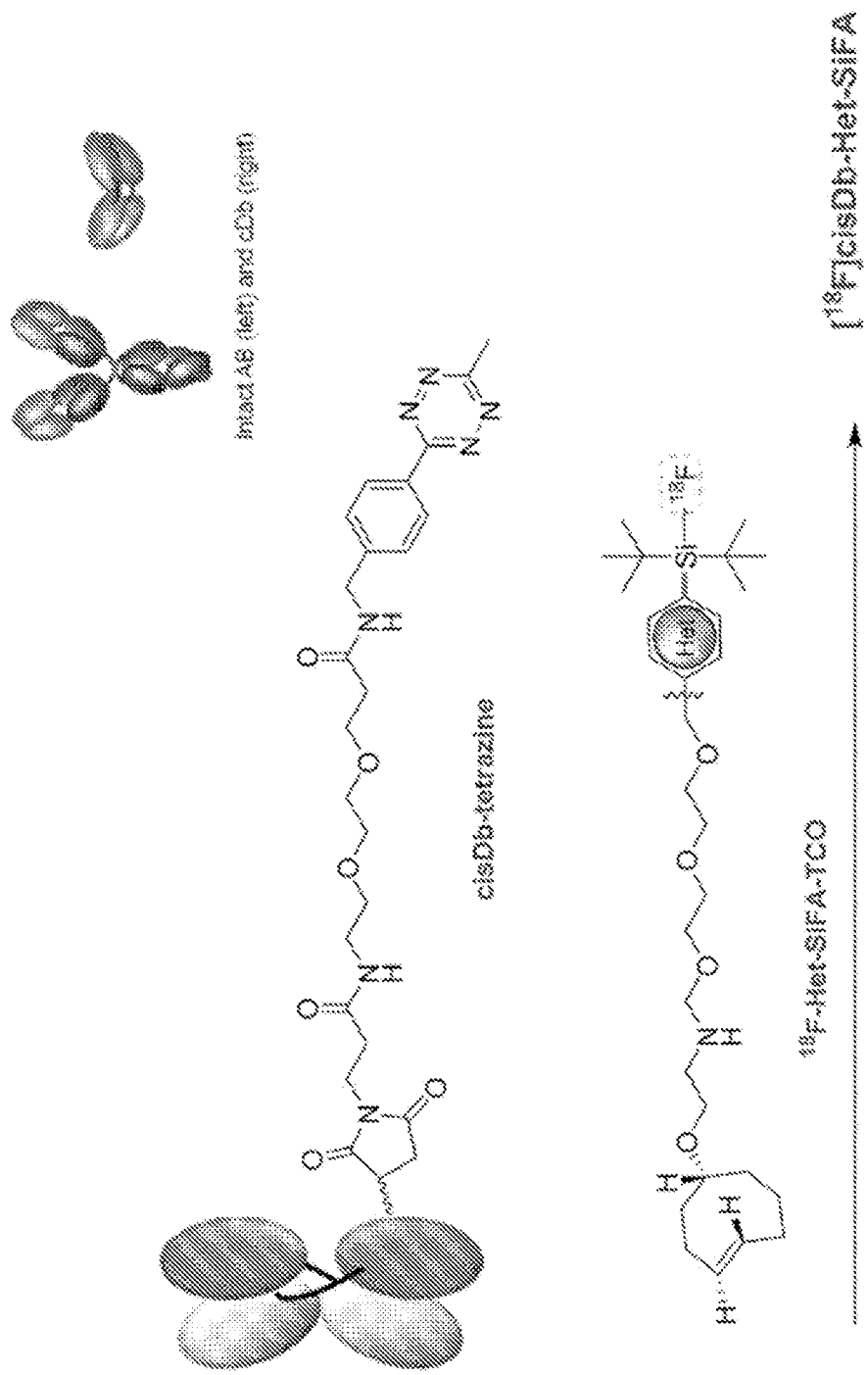
FIG. 5 depicts antibody fragment-based imaging of PSCA-expressing prostate cancer, specifically engineered PSCA-specific antibody fragments, namely Cys-diabodies (cDb), retaining high selective binding of the parental antibody yet exhibiting rapid blood clearance, making them suitable for labeling with short-lived radionuclides such as positron emitting Fluorine-18.

TCO-silicon-fluoride-acceptors are used for example in antibody fragment-based imaging of PSCA-expressing prostate cancer (FIG. 5). Engineered PSCA-specific antibody fragments, namely Cys-diabodies (cDb), retaining high selective binding of the parental antibody yet exhibiting rapid blood clearance, are suitable for labeling with short-lived radionuclides such as positron emitting Fluorine-18, which is achieved by click chemistry attachment of a cisDb-tetrazine derivative to a TCO-heteroaromatic silicon-fluoride-acceptor.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula 3:

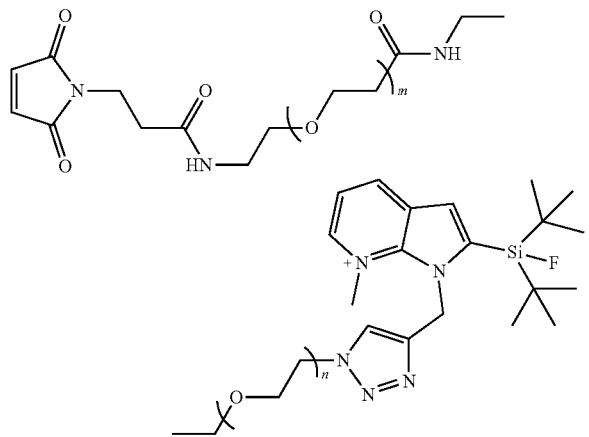

(Formula 3)

wherein,

F is $^{19}$F or $^{18}$F; and m and n are each independently an integer selected from the group consisting of 0, 1, 2, 3, 4, 5 and 6.

2. A method for imagining a biological target by PET scanning, comprising introducing into the biological target an imaging agent comprising a compound of claim 1, wherein F is $^{18}$F, that is conjugated to a ligand for the biological target.

3. The method of claim 2, wherein the ligand is a peptide, a protein, an enzyme, an antibody, or a small molecule.

4. The method of claim 2, wherein the conjugation comprises a maleimide-thiol adduct, or a click chemistry adduct.

5. A kit for $^{18}$F-labeling of a compound of claim 1, the kit comprising a compound of Formula 3, wherein F is $^{19}$F, and an $^{18}$F isotopic exchange reagent.

6. A method for imaging a biological target by PET scanning, comprising introducing into the biological target an imaging agent comprising a compound of Formula 4:

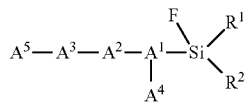

Formula 4 wherein,

F is $^{18}$F;

$A^1$ is a monocyclic or bicyclic heteroaryl ring optionally substituted with 1-4 $R^a$ groups;

$A^2$ is a linker;

$A^3$ is a moiety that chemically conjugates or bioconjugates $A^2$ to $A^5$;

$A^4$ is a moiety comprising a polar auxiliary that optionally contains a charge;

$A^5$ is a moiety comprising a disease targeting molecule or biomolecule;

$R^a$ is, at each independent occurrence, F, Cl, Br, I, CN, NO$_2$, OR$^c$, OC(=O)R$^c$, OC(=O)OR$^c$, OC(=O)NR$^c$R$^d$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)$_2$R$^d$, NR$^c$S(=O)$_2$NR$^d$R$^e$, SR$^c$, S(=O)R$^c$, S(=O)$_2$R$^c$, and S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents that are F, Cl, Br, I, CN, NO$_2$, OR$^c$, OC(=O)R$^c$, OC(=O)OR$^c$, OC(=O)NR$^c$R$^d$, C(=O)R$^c$, C(=O)NR$^c$R$^d$, C(=O)OR$^c$, NR$^c$R$^d$, NR$^c$C(=O)R$^d$, NR$^c$C(=O)OR$^d$, NR$^c$C(=O)NR$^d$R$^e$, NR$^c$S(=O)$_2$R$^d$, NR$^c$S(=O)$_2$NR$^d$R$^e$, SR$^c$, S(=O)R$^c$, S(=O)$_2$R$^c$, or S(=O)$_2$NR$^c$R$^d$, or independent $R^a$ groups can optionally be joined to form additional rings;

R$^c$, R$^d$ and R$^e$ are, at each independent occurrence, H, or optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, and any of R$^c$, R$^d$ or R$^e$ can optionally be joined to form additional rings;

wherein the Si is bonded to a carbon of $A^1$;

$A^1$ is not 1,2,3-triazolyl; and $R^1$ and $R^2$ are each independently an alkyl group;

that is conjugated to a ligand for the biological target.

7. The method of claim 6, wherein $A^1$ is an optionally substituted furanyl, an optionally substituted pyridyl, an optionally substituted pyrazinyl, an optionally substituted pyrimidinyl, an optionally substituted pyridazinyl, an optionally substituted thienyl, an optionally substituted pyrrolyl, an optionally substituted imidazolyl, an optionally substituted thiazolyl, an optionally substituted oxazolyl, an optionally substituted pyrazolyl, an optionally substituted isothiazolyl, an optionally substituted 1,2,4-triazolyl, an optionally substituted 1,3,4-triazolyl, an optionally substituted tetrazolyl, an optionally substituted 1,2,3-thiadiazolyl, an optionally substituted 1,2,3-oxadiazolyl, an optionally substituted 1,3,4-thiadiazolyl, an optionally substituted 1,3,4-oxadiazolyl, the substituted indolyl whose nitrogen is protected with the amino protecting group, an optionally substituted indolinyl, an optionally substituted quinolyl, an optionally substituted tetrahydroquinolyl, an optionally substituted 1,2,3,4-tetrahydroisoquinolyl, an optionally substituted cinnolinyl, an optionally substituted quinoxalinyl, an optionally substituted quinazolinyl, an optionally substituted phthalazinyl, an optionally substituted 1,8-naphthyridinyl, an optionally substituted 1,4-benzodioxanyl, an optionally substituted coumarin, an optionally substituted dihydrocoumarin, an optionally substituted 1,5-naphthyridinyl, an optionally substituted benzofuryl, an optionally substituted 2,3-dihydrobenzofuryl, an optionally substituted 1,2-benzisoxazolyl, an optionally substituted benzothienyl, an optionally substituted benzoxazolyl, an optionally substituted benzothiazolyl, an optionally substituted purinyl, an optionally substituted benzimidazolyl, an optionally substituted benzotriazolyl, an optionally substituted thioxanthinyl, an optionally substituted carbazolyl, an optionally substituted carbolinyl, an optionally substituted acridinyl, an optionally substituted pyrrolizidinyl, or an optionally substituted quinolizidinyl.

8. The method of claim 7, wherein $A^1$ is indolyl, 7-azaindolyl, benzothiophenyl, furanyl, pyrrolyl, pyrazolyl, imidazolyl, or pyridinyl.

9. The method of claim 6, wherein $R^1$ and $R^2$ are tert-butyl groups.

10. The method of claim 6, wherein $A^2$ comprises at least one of an unsubstituted alkylene, an unsubstituted polyethylene glycol (PEG) ether, or a bisubstituted triazolyl.

11. The method of claim 6, wherein $A^3$ is an ester, an amide, a maleimide-thiol adduct, or a click chemistry adduct.

12. The method of claim 6, wherein $A^4$ is moiety comprising a PEG chain, a polar group, or a charged group.

13. The method of claim 6, wherein:
$A^2$ comprises at least one of an unsubstituted alkylene, an unsubstituted polyethylene glycol (PEG) ether, or a bisubstituted triazolyl;
$A^3$ is an alkyne, an azide, N-hydroxysuccinimide (NHS) ester or a maleimide;
$A^4$ is a PEG chain, a polar group, or a charged group;
$R^1$ and $R^2$ are tert-butyl groups.

14. The method of claim 6, wherein the ligand is a peptide, a protein, an enzyme, an antibody, or a small molecule.

15. The method of claim 6, wherein the conjugation comprises a maleimide-thiol adduct, or a click chemistry adduct.

* * * * *